United States Patent [19]

Hardy

[11] 4,358,609
[45] Nov. 9, 1982

[54] PROCESS FOR THE RECOVERY OF CARBOXYLIC ACID FROM MIXTURES CONTAINING GLYCOL ESTERS DERIVED FROM THESE ACIDS

[75] Inventor: Nicolas Hardy, Jemeppe-sur-Sambre, Belgium

[73] Assignee: Propylox (Société Anonyme), Brussels, Belgium

[21] Appl. No.: 192,830

[22] Filed: Oct. 1, 1980

[30] Foreign Application Priority Data

Oct. 1, 1979 [FR] France .............................. 79 24581

[51] Int. Cl.³ .......................... B01D 3/36; B01D 3/40
[52] U.S. Cl. ..................................... 562/606; 203/60; 203/61; 203/63; 203/67; 260/415; 260/419; 562/607; 562/608; 562/609
[58] Field of Search ............................... 562/606-609, 562/523, 544-549, 593; 260/415, 419; 203/15, 16, 50, 57, 67-70, 60-66

[56] References Cited

U.S. PATENT DOCUMENTS

| 3,718,545 | 2/1973 | Horlenko | 203/15 |
| 3,878,241 | 4/1975 | Müller | 203/16 |
| 3,951,755 | 4/1976 | Sartorius et al. | 203/16 |
| 4,091,039 | 5/1978 | Scheibel | 562/606 |

FOREIGN PATENT DOCUMENTS 49901 11/1966 United Kingdom .

*Primary Examiner*—Frank Sever
*Attorney, Agent, or Firm*—Spencer & Kaye

[57] ABSTRACT

A process for the recovery of carboxylic acids from mixtures containing glycol esters derived from these acids. The process comprises reacting these mixtures at boiling with water to form carboxylic acid and entraining the carboxylic acid formed by means of the water by azeotropic distillation, so as to separate off a mixture of carboxylic acid and water. This mixture is subjected to extractive distillation by means of an organic solvent which is insoluble in water and in which water is insoluble. A mixture of water and organic solvent is thereby separated from a solution of carboxylic acid in the organic solvent.

14 Claims, 3 Drawing Figures

PROCESS FOR THE RECOVERY OF CARBOXYLIC ACID FROM MIXTURES CONTAINING GLYCOL ESTERS DERIVED FROM THESE ACIDS

BACKGROUND OF THE INVENTION

The present invention relates to a process for the recovery of carboxylic acids from mixtures containing glycol esters derived from these acids.

It relates more particularly to the recovery of carboxylic acids present in the heavy residues which are obtained in the epoxidation of olefines by means of the corresponding percarboxylic acids, and which contain glycol esters of these carboxylic acids.

During the epoxidation of olefines by means of peroxide compounds, such as percarboxylic acids, a mixture is obtained which contains the olefine oxide, the carboxylic acid, the solvent, if appropriate, the unconverted reactants and also various by-products including esters of the carboxylic acid. These esters are probably formed by various secondary reactions involving the olefine oxide produced and the carboxylic acid corresponding to the percarboxylic acid employed. These secondary reactions can take place both in the epoxidation reactor and in the installation used for separating the mixture originating from the epoxidation reactor. Thus, during the epoxidation of propylene with perpropionic acid, the formation of substantial amounts of propylene glycol mono- and di-propionates is observed, and this leads to a loss of reactants.

In an attempt to overcome this disadvantage, a process has been proposed, the object of which is essentially to obtain propylene glycol dipropionate (Belgian Pat. No. 841,201, filed on Apr. 28, 1976 in the names of BAYER AG and DEGUSSA). Obviously, this process does not make it possible to reduce the loss of reactants and exhibits the disadvantage of the inevitable production of propylene glycol dipropionate.

SUMMARY OF THE INVENTION

The object of the invention is to provide a process for the recovery of carboxylic acids from mixtures containing glycol esters derived from these acids, which process avoids the loss of reactants and the inevitable formation of a by-product.

DETAILED DESCRIPTION OF THE INVENTION

Figure 1:
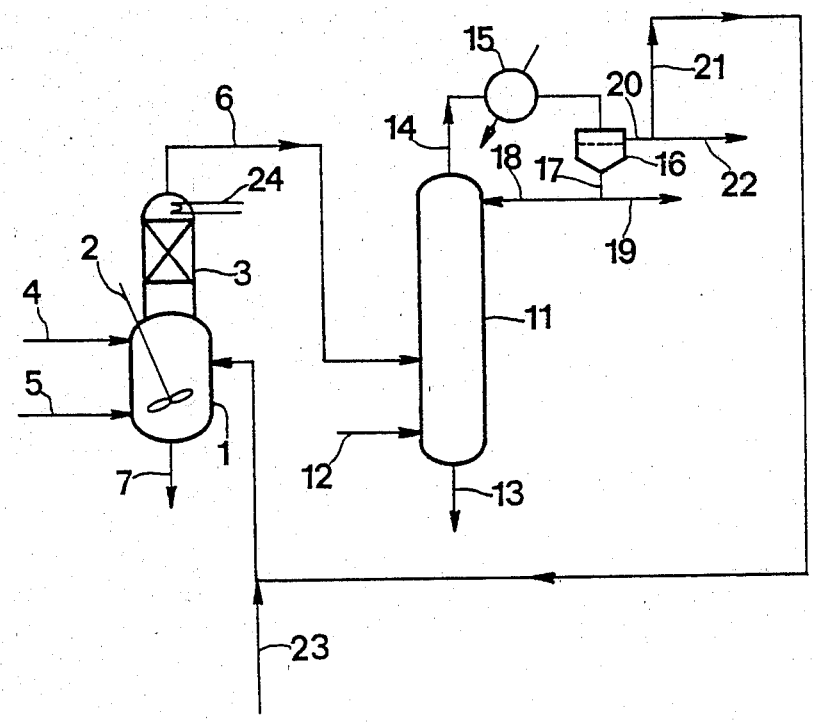
FIGS. 1, 2, and 3 are schematic diagrams of apparatuses used to carry out the process of the present invention.

For this purpose, the invention relates to a process for the recovery of carboxylic acids from mixtures containing glycol esters derived from these acids, by hydrolysis of these esters, in accordance with which the mixtures containing the esters are reacted at the boil with water, and the carboxylic acid thus formed is entrained by means of the water by azeotropic distillation, and in accordance with which the mixture of carboxylic acid and water thus obtained is subjected to extractive distillation by means of an organic solvent which is insoluble in water and in which water is insoluble, so as to separate a mixture of water and organic solvent from a solution of carboxylic acid in the organic solvent.

The process according to the invention is applicable to mixtures containing mono- and/or di-esters of carboxylic acids and of various types of glycols. It is suitable for the treatment of mixtures containing esters derived from carboxylic acids containing from 1 to 8 carbon atoms and glycols containing from 2 to 4 carbon atoms. The process according to the invention is preferably applied to mixtures containing esters which are derived from carboxylic acids containing 1 to 4 carbon atoms and glycols containing 3 or 4 carbon atoms, and which can be substituted by halogen atoms, such as chlorine. Very good results have been obtained by applying the process according to the invention to mixtures contaning at least one compound chosen from amongst optionally chlorinated propylene glycol monopropionate and dipropionate.

The total amount of esters present in the mixtures to be treated according to the invention can vary within wide limits, depending on the origin of the mixtures and the preliminary concentration processes to which they may have been subjected. In general, the mixtures contain more than 5% of their weight of esters.

The mixtures to be treated according to the invention usually contain other constituents, such as carboxylic acids, glycols and their oligomers, and solvents.

The carboxylic acids which can be present in the mixtures to be treated according to the invention can be of various types. They can be of the same type or of different types. In general, they are carboxylic acids containing from 1 to 8 carbon atoms. Most frequently, they mainly consist of the carboxylic acids from which the esters are derived. Small amounts of other carboxylic acids can be present, generally in amounts of less than 10% of the total weight of carboxylic acids. The total amount of carboxylic acids in the mixtures to be treated according to the invention can vary within wide limits and depends on the origin of these mixtures. It is generally less than 90% of the weight of the mixtures.

The glycols and their oligomers which can be present in the mixtures to be treated according to the invention can be of various types. They generally contain from 2 to 4 substituted or unsubstituted carbon atoms. In general, they are essentially of the same type as those from which the esters contained in the mixtures to be treated are derived. The total amount of glycols and their oligomers is generally less than 80% of the weight of the mixtures.

The solvents which may be present in the mixtures to be treated can be of very diverse types. These solvents are generally chosen from amongst ethers, hydrocarbons substituted by nitro groups, halogenohydrocarbons, unsubstituted hydrocarbons, nitriles and mixtures thereof.

The mixtures to be treated generally contain less than 20% by weight of solvent and preferably less than 10% by weight of solvent.

Finally, the mixtures to be treated can also contain various other products in amounts which do not generally exceed 15% of their weight. The nature of these products of course depends on the origin of the mixtures. In general, they are catalyst residues and also various by-products of the reactions which have led to the formation of these mixtures. Thus, if the invention is applied to mixtures containing optionally chlorinated propylene glycol monopropionate and/or dipropionate, it also makes it possible to recover the organic acid from the propionates of chloropropanol or chloroethanol which are generally present in these mixtures.

The process according to the invention is particularly applicable to the treatment of mixtures, based on glycol esters, originating from the epoxidation of olefines with the aid of percarboxylic acids. In these processes, after the olefine oxide and the unconverted olefine have been recovered, mixtures are obtained which contain esters derived from the carboxylic acids, glycols, carboxylic acids and, if appropriate, solvent, in proportions which can vary depending on whether all or part of the solvent, and, if appropriate, of the carboxylic acid, has been removed beforehand.

If the proportion of esters in the mixtures to be treated is less than 5% by weight, or if the proportion of solvents exceed 10% by weight, the solvent and, if appropriate, part of the carboxylic acid are generally evaporated off beforehand so as to increase the proportion of esters to more than 5%, and preferably to more than 10%, by weight, or to reduce the proportion of solvent to less than 10% by weight, before treating the mixtures according to the invention. Various evaporators which are in themselves known can be used for this purpose, in particular thermosiphon stills, film evaporators or distillation columns. This operation can be carried out in several steps, preferably combining the various apparatuses. This vaporisation is generally carried out at temperatures between 300 and 420 K. and at pressures between 0.01 and 2 bars.

The hydrolysis of the esters is carried out in a reactor in which the temperature and the pressure are such that the reaction mixture is kept at the boil. The temperature is generally between 300 and 450 K. and the pressure is generally between 0.05 and 10 bars. Preferably, temperatures of 310 to 400 K. and pressures of 0.8 to 5 bars are used. The water required is used in the liquid form or in the form of steam. The water is advantageously introduced into the reactor in the form of steam. The amounts of water used are preferably chosen so as to hydrolyse the esters as completely as possible and to entrain the largest possible amounts of the carboxylic acids formed by the reaction and also of the carboxylic acids which may be present in the starting mixtures. In general, the water is used in amounts such that the weight ratio of the water to all the carboxylic acids present (that is to say the acids already present in the mixtures to be treated and the acids formed by the reaction) is equal to or greater than the ratio of water to carboxylic acid in the azeotrope. Thus, when the carboxylic acid is propanoic acid or butanoic acid, this ratio is at least about 5:1. For economic reasons, the amount of water used does not generally exceed 10 times the amount of water required for the distillation of the water/carboxylic acid azeotropes.

Water of various origins can be used for the hydrolysis and the azeotropic distillation of the carboxylic acid. Thus, it is possible to use fresh water. If the process of the invention is coupled to the epoxidation of olefines by means of peracids, it is advantageous to use the waste water obtained during the concentration of the aqueous effluents from the manufacture of the peracid. This waste water essentially consists of water and contains very small amounts of catalysts (in general sulphuric acid) and of carboxylic acid, which do not generally exceed 2% of their weight.

The hydrolysis reaction is generally assisted by the presence of acid catalysts, which can be of very diverse types. Sulphuric acid is a suitable catalyst. In view of the fact that the mixtures to be treated most frequently contain free carboxylic acids and/or acid catalyst residues (in particular if they originate from an installation for the epoxidation of olefines with peracids), it is generally not essential to add acid catalysts.

The hydrolysis reaction can be carried out discontinuously or, preferably, continuously, in any type of reactor which is suitable for this kind of reaction and which is made of materials resistant to the reaction mixture. If the reaction is carried out continuously, it is possible to use reactors in a cascade.

If the reaction is carried out continuously, part of the hydrolysis reaction mixture is purged in order to remove the glycols formed during the hydrolysis reaction, and also their oligomers. This mixture only contains very small amounts of esters and of carboxylic acids and usually contains, apart from the glycols and their oligomers, water, acid catalysts, if appropriate, and various by-products. The purge is generally incinerated.

The hydrolysis reaction is carried out under conditions such that the carboxylic acids are entrained by the steam and distilled azeotropically.

The vapour phase containing the carboxylic acids and the water is subjected, according to the invention, to extractive distillation by means of an organic solvent which is insoluble in water and in which water is insoluble. The expression "solvents which are insoluble in water" is understood as denoting solvents of which the solubility in water is less than 10% and preferably less than 5%. The expression "solvents in which water is insoluble" is understood as denoting solvents in which water has a solubility of less than 5% and preferably less than 2%. These solvents must also readily dissolve the carboxylic acid, and the solubility of the latter in the solvent must be at least 5%. These solvents are generally chosen from amongst carboxylic acid esters, ethers, nitriles, halogenohydrocarbons, unsubstituted hydrocarbons, hydrocarbons substituted by nitro groups, non-acid esters of carboxylic, nitric and phosphoric acids, and mixtures thereof.

Suitable solvents which may be mentioned are benzene, toluene, cyclohexane, decane, heptane, petroleum ether, 1,2-dichloropropane, 1,1,2,2-tetrachloroethane, 1,2-dichloroethane, pentachloroethane, trichloroethylene, tetrachloroethylene, nitrobenzene, chlorobenzene and cyclohexyl chloride. Particularly good results have been obtained with 1,2-dichloroethane, 1,2-dichloropropane, benzene and mixtures thereof.

If the process according to the invention is coupled with a process for the epoxidation of olefines with the aid of percarboxylic acids, it is advantageous to use the same solvent as that used for the epoxidation.

The extractive distillation by means of organic solvent can be carried out in accordance with any technique which is in itself known. In general, the distillation is carried out at temperatures between 300 and 450 K. and under pressures between 0.1 and 5 bars. The new gas phase which is obtained and which contains water and organic solvent, generally in a virtually pure state, is condensed and separated by decantation in accordance with any technique which is in itself known. The aqueous fraction thus obtained is discarded and preferably only part of the organic solvent is recycled to the distillation column. In this case, in fact, the surplus solvent is advantageously made available for recovering the carboxylic acid by liquid-liquid extraction from aqueous phases, such as, for example, those produced during the generation of percarboxylic acid.

The carboxylic acids, mixed with the solvent if appropriate, are collected at the foot of the distillation column.

If, before being hydrolysed, the mixtures to be treated according to the invention are vaporised so as to separate therefrom at least part of the solvent and, if appropriate, part of the carboxylic acid, the solvent-rich vapour phase separated off in this way is particularly advantageously used to carry out the subsequent extractive distillation of the carboxylic acids from their mixtures with water.

The process according to the invention is particularly applicable to the treatment of the heavy residues, containing esters such as glycol mono- and di-propionates, obtained in the processes for the manufacture of olefine oxides with the aid of percarboxylic acids, such as perpropionic acid, which processes are described in Belgian Pat. No. 847,664, filed on Oct. 27, 1976 in the names of BAYER AG and DEGUSSA, and Belgian Pat. No. 838,068, filed on Jan. 30, 1976 in the name of INTEROX CHEMICALS LTD.

Figure 2:
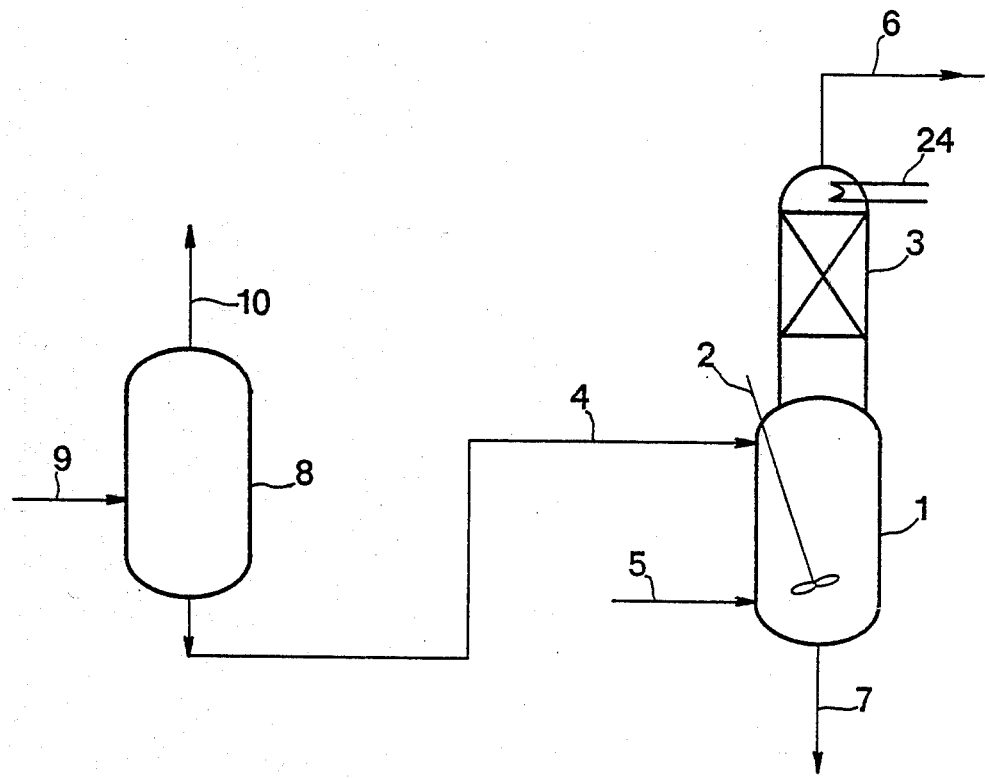
Figure 3:
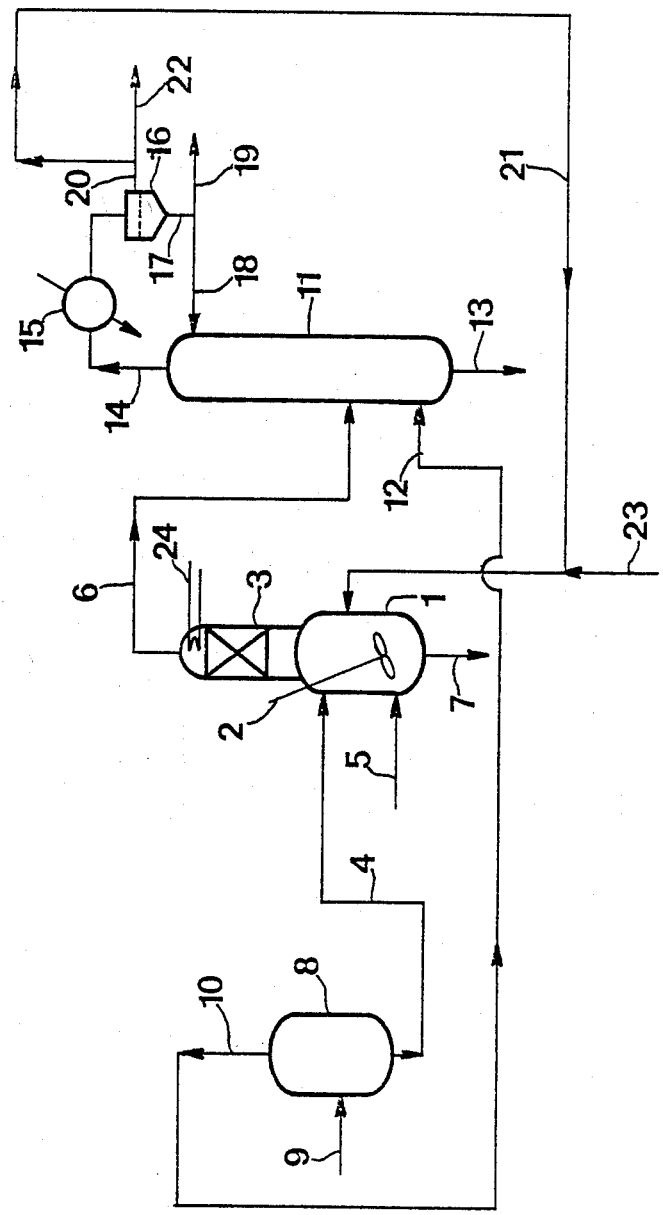

The process according to the invention can be carried out in apparatuses such as those shown schematically in FIGS. 1, 2 and 3 of the attached drawings, which relate to particular practical embodiments.

According to the process shown schematically in FIG. 1, a mixture containing esters is introduced via 4 into the reactor 1, which is provided with heating means (not shown) and a stirrer 2 and is surmounted by a distillation column 3 equipped with a partial condenser 24. Steam is introduced via 5 into the reactor 1. A vapour phase containing the carboxylic acid and water is drawn off via 6. A purge, which contains the glycols and their oligomers and water, is drawn off via 7. The vapour phase containing the carboxylic acid and water, and obtained via 6, is subjected to extractive distillation in the distillation column 11. The distillation column 11 is fed via 12 with a vapour phase rich in organic solvent. Carboxylic acid, generally mixed with the solvent, is collected via 13. At the head of the distillation column, a vapour phase containing water and solvent is collected via 14 and is condensed at 15 and sent to the decanter 16 in order to separate the aqueous fraction, via 20, from the organic fraction, which contains the solvent, via 17. If the density of the aqueous fraction is greater than that of the organic fraction, the withdrawals are reversed. Part of the aqueous fraction can be sent via 21 into the hydrolysis reactor; the remainder is discarded via 22. Additional steam is supplied via 23. At least part of the organic fraction, which contains the solvent, is recycled to the distillation column 11, where it constitutes the reflux. The remainder is collected via 19 and can be used in the manufacture of the peracid for extracting the peracid from its aqueous solutions or for extracting the carboxylic acid from its aqueous solutions, or it can also be used as reflux for the distillation column 3 in the case where the partial condenser 24 is absent (not shown).

According to the process shown schematically in FIG. 2, a composition containing esters and a solvent is introduced via 9 into an evaporator 8. At least part of the solvent is vaporised in the evaporator and collected via 10. The liquid mixture which contains the esters is sent via 4 into an identical apparatus to that shown schematically in FIG. 1.

The process shown schematically in FIG. 3 constitutes a combination of the processes shown schematically in FIGS. 1 and 2, according to which combination the solvent-rich vapour collected from the evaporator 8 via 10 is used and is sent via 12 to the extractive distillation column 11.

A practical embodiment is provided below in order to illustrate the invention without thereby limiting its scope.

EXAMPLE

This example relates to the treatment of a mixture containing propylene glycol mono- and di-propionates. This mixture is obtained after the propylene, the epoxypropane and part of the 1,2-dichloroethane have been separated from the reaction mixture originating from the epoxidation of propylene with a solution of perpropionic acid in dichloroethane.

The treatment is carried out in the apparatus shown schematically in FIG. 3. The compositions of the product streams in the installation are given in Table I below.

About 119 kg of mixture are used per hour. The mixture is evaporated in a 2-stage evaporation section (8). The first evaporation stage operates at an overhead temperature of 364 K. under a pressure of 0.55 bar. The second evaporation stage, which is not shown in FIG. 4, operates at an overhead temperature of 345 K. under a pressure of 0.1 bar.

The liquid collected at the foot of the second evaporation stage, at a rate of 3 kg/hour, is sent to the hydrolysis reactor (1) in which it is treated at atmospheric pressure with 11 kg/hour of steam. The overhead temperature of the hydrolyser (3) is about 373 K. 1.5 kg of residues per hour are discarded at the foot of the hydrolyser.

The gas phase collected at the head of the hydrolyser is sent into the extractive distillation column (11) at the same time as the dichloroethane collected at the head of the first evaporation stage. 85 kg/hour of a solution of propionic acid in 1,2-dichloroethane are collected at the foot of the column (11).

The aqueous phase discharged through the pipe (22) contains less than 5 g/kg of propionic acid, and the organic phase discharged through the pipe (19) consists of 28 kg/hour of virtually pure 1,2-dichloroethane.

A comparison of the streams in the pipes (4) and (7) demonstrates the efficiency of the propionic acid recovery carried out by the process.

TABLE I

| | Composition of the streams in g/kg | | | | | |
|---|---|---|---|---|---|---|
| | Stream 9 | Stream 10 | Stream 4 | Stream 7 | Stream 6 | Stream 13 |
| water | 0.63 | — | — | 608 | 825 | 1.5 |
| sulphuric acid | 0.09 | — | 35 | 70 | — | — |
| 1,2-dichloroethane | 733 | 769 | 20 | 20 | 10 | 653 |
| propionic acid | 232 | 220 | 171 | 83 | 150 | 315 |
| various impurities | 23.95 | 7.7 | 67 | 8.7 | 12.5 | 45.27 |
| propylene glycol propionates | 7.8 | 2.8 | 600 | 50 | 1.1 | 3.2 |

TABLE I-continued

| | Composition of the streams in g/kg | | | | | |
|---|---|---|---|---|---|---|
| | Stream 9 | Stream 10 | Stream 4 | Stream 7 | Stream 6 | Stream 13 |
| propylene glycol and dimers | 2.53 | 0.5 | 92 | 160.3 | 1.4 | 0.03 |

I claim:

1. Process for the recovery of carboxylic acids from a mixture containing glycol esters derived from these acids, by hydrolysis of these esters, said mixture being obtained during the epoxidation of an olefin with the aid of percarboxylic acid comprising:
   (a) reacting the mixture containing the esters at the boil with water to form carboxylic acid,
   (b) entraining the carboxylic acid thus formed by means of the water, by azeotropic distillation to form a mixture containing essentially water and substantially all of the carboxylic acid present, and
   (c) subjecting the mixture of carboxylic acid and water thus obtained to extractive distillation by adding an organic solvent which is insoluble in water and in which water is insoluble, said organic solvent being selected from the group consisting of carboxylic acid esters, ethers, nitriles, halogenated hydrocarbons, unsubstituted hydrocarbons, hydrocarbons substituted by nitro groups, non-acid esters of carboxylic, nitric and phosphoric acid, and mixtures thereof, so as to separate a mixture of water and organic solvent from a substantially anhydrous solution of carboxylic acid in the organic solvent.

2. Process according to claim 1, wherein the mixture used contains esters derived from carboxylic acids containing 1 to 4 carbon atoms and glycols containing 3 or 4 carbon atoms.

3. Process according to claim 1 or 2, wherein the mixture used contains from 5 to 80% by weight of esters.

4. Process according to claim 1 or 2, wherein the mixture used contains carboxylic acids.

5. Process according to claim 1 or 2, wherein the mixture used also contains glycols or their oligomers.

6. Process according to claim 1 or 2, wherein the mixture used also contains a solvent.

7. Process according to claim 1 or 2, wherein the mixture which is reacted is obtained from a mixture which contains a solvent, and said mixture which contains a solvent is subjected to vaporization to vaporize the solvent so as to obtain (i) a fraction containing solvent, and (ii) said mixture which is reacted and which contains the esters.

8. Process as defined in claim 1, wherein the solvent is selected from the group consisting of benzene, toulene, cyclohexane, decane, heptane, petroleum ether, 1,2-dichloropropane, 1,1,2,2-tetrachloroethane, 1,2-dichloroethane, pentachloroethane, trichloroethylene, tetrachloroethylene, nitrobenzene, chlorobenzene, cyclohexyl chloride, and mixtures thereof.

9. Process as claimed in claim 1, wherein the solvent is selected from the group consisting of 1,2-dichloroethane, 1,2-dichloropropane, benzene and mixtures thereof.

10. Process as defined in claim 1, wherein the solvent is one in which water has a solubility of less than 2%.

11. Process as defined in claim 1, wherein the esters are derived from carboxylic acids containing 1 to 8 carbon atoms and glycols containing from 2 to 4 carbon atoms.

12. Process for the recovery of carboxylic acids from a starting mixture containing (i) an organic solvent which is insoluble in water and in which water is insoluble and (ii) glycol esters derived from these acids, and obtained during epoxidation of an olefin with the aid of percarboxylic acid, by hydrolysis of the esters, comprising the following steps:
   (a) vaporizing the organic solvent in the starting mixture in a manner to obtain (i) a fraction containing the solvent in vapor form and (ii) a reaction mixture containing the esters,
   (b) reacting by boiling the reaction mixture containing the esters with water to form carboxylic acid,
   (c) entraining the carboxylic acid thus formed, by means of the water, by azeotropic distillation to form a mixture containing essentially water and substantially all of the carboxylic acid present, and
   (d) subjecting the mixture of carboxylic acid and water thus obtained to an extractive distillation by means of the organic solvent in vapor form obtained in step (a), said organic solvent being selected from the group consisting of carboxylic acid esters, ethers, nitriles, halogenated hydrocarbons, unsubstituted hydrocarbons, hydrocarbons substituted by nitro groups, non-acid esters of carboxylic, nitric and phosphoric acid, and mixtures thereof, in a manner to separate a mixture of water and organic solvent from a substantially anhydrous solution of carboxylic acid in the organic solvent.

13. Process for the recovery of carboxylic acids from a mixture containing glycol esters derived from these acids and obtained during epoxidation of an olefin with the aid of percarboxylic acid, by hydrolysis of these esters, comprising the following steps:
   (a) reacting by boiling the mixture containing the esters with residual water obtained during concentration of the aqueous effluents from the manufacture of the peracid and containing essentially water, and very small quantities of catalysts and of carboxylic acid to form carboxylic acid,
   (b) entraining the carboxylic acid thus formed, by means of the water, by azeotropic distillation, to form a mixture containing essentially water and substantially all of the carboxylic acid, and
   (c) subjecting the mixture of carboxylic acid and water thus obtained to an extractive distillation by adding an organic solvent insoluble in water and in which water is insoluble, said solvent being selected from the group consisting of carboxylic acid esters, ethers, nitriles, halogenated hydrocarbons, unsubstituted hydrocarbons, hydrocarbons substituted by nitro groups, non-acid esters of carboxylic, nitric and phosphoric acid, and mixtures thereof, in a manner to separate a mixture of water and organic solvent from a substantially anhydrous solution of carboxylic acid in the organic solvent.

14. Process for recovery of carboxylic acids from a starting mixture containing (i) an organic solvent insoluble in water and in which water is insoluble and (ii) glycol esters derived from these acids and obtained during epoxidation of an olefin with the aid of percarboxylic acid, by hydrolysis of these esters, comprising the following steps:
(a) vaporizing the organic solvent in the starting mixture in a manner to obtain (i) a fraction containing the solvent in vapor form and (ii) a reaction mixture containing the esters,
(b) reacting by boiling the reaction mixture containing the esters with residual water obtained during concentration of aqueous effluents from the manufacture of the peracid and containing essentially water, and very small quantities of catalysts and of carboxylic acid to form carboxylic acid,
(c) entraining the carboxylic acid thus formed, by means of the water, by azeotropic distillation to form a mixture containing essentially water and substantially all of the carboxylic acid present, and
(d) subjecting the mixture of carboxylic acid and of water thus obtained to an extractive distillation by means of the organic solvent in vapor form obtained in step (a), said solvent being selected from the group consisting of carboxylic acid esters, ethers, nitriles, halogenated hydrocarbons, unsubstituted hydrocarbons, hydrocarbons substituted by nitro groups, non-acid esters of carboxylic, nitric and phosphoric acid, and mixtures thereof, in a manner to separate a mixture of water and of organic solvent from a substantially anhydrous solution of carboxylic acid in the organic solvent.

* * * * *